United States Patent [19]
Berbeé et al.

[11] Patent Number: 4,466,286
[45] Date of Patent: Aug. 21, 1984

[54] SCANNER FOR SCANNING AN OBJECT BY MEANS OF ULTRASONIC RADIATION

[75] Inventors: Hubertus J. Berbeé, Rozenburg; Hendrik J. Voûte, Nootdorp; Johannes M. Thijssen, Nijmegen, all of Netherlands

[73] Assignee: N.V. Optische Industrie "de Oude Delft", Netherlands

[21] Appl. No.: 363,908

[22] Filed: Mar. 31, 1982

[30] Foreign Application Priority Data

Apr. 8, 1981 [NL] Netherlands ............... 8101744

[51] Int. Cl.$^3$ ............................................. G01N 29/00
[52] U.S. Cl. ....................................... 73/629; 73/633; 73/642
[58] Field of Search ............... 73/628, 629, 641, 642, 73/633; 128/660

[56] References Cited

U.S. PATENT DOCUMENTS 3,245,251 4/1966 von Ardenne ................. 73/642
3,529,465 9/1970 Kleesattel et al. .............. 73/629
4,185,501 1/1980 Proudian et al. ............... 73/641
4,194,510 3/1980 Proudian ....................... 73/629

Primary Examiner—Gerald Goldberg
Assistant Examiner—John E. Chapman, Jr.
Attorney, Agent, or Firm—Louis E. Marn; Elliot M. Olstein

[57] ABSTRACT

A scanner for periodically scanning an object to be examined with a beam of ultrasonic radiation. A transducer mounted within a housing emits a beam of ultrasonic radiation. The beam is guided and deflected respectively to a continuously rotating scanning reflector which is disposed opposite a stationary object reflector, from which the beam is directed to the object. The beam propagation path further includes a first focussing member adapted to focus the beam to a focal point within the housing, and a second focussing member adapted to focus the beam to a focal point within the object. In a preferred embodiment the first focussing member can be selectively adjusted. Thereby the focal area of the beam in the object can be conveniently shifted.

20 Claims, 2 Drawing Figures

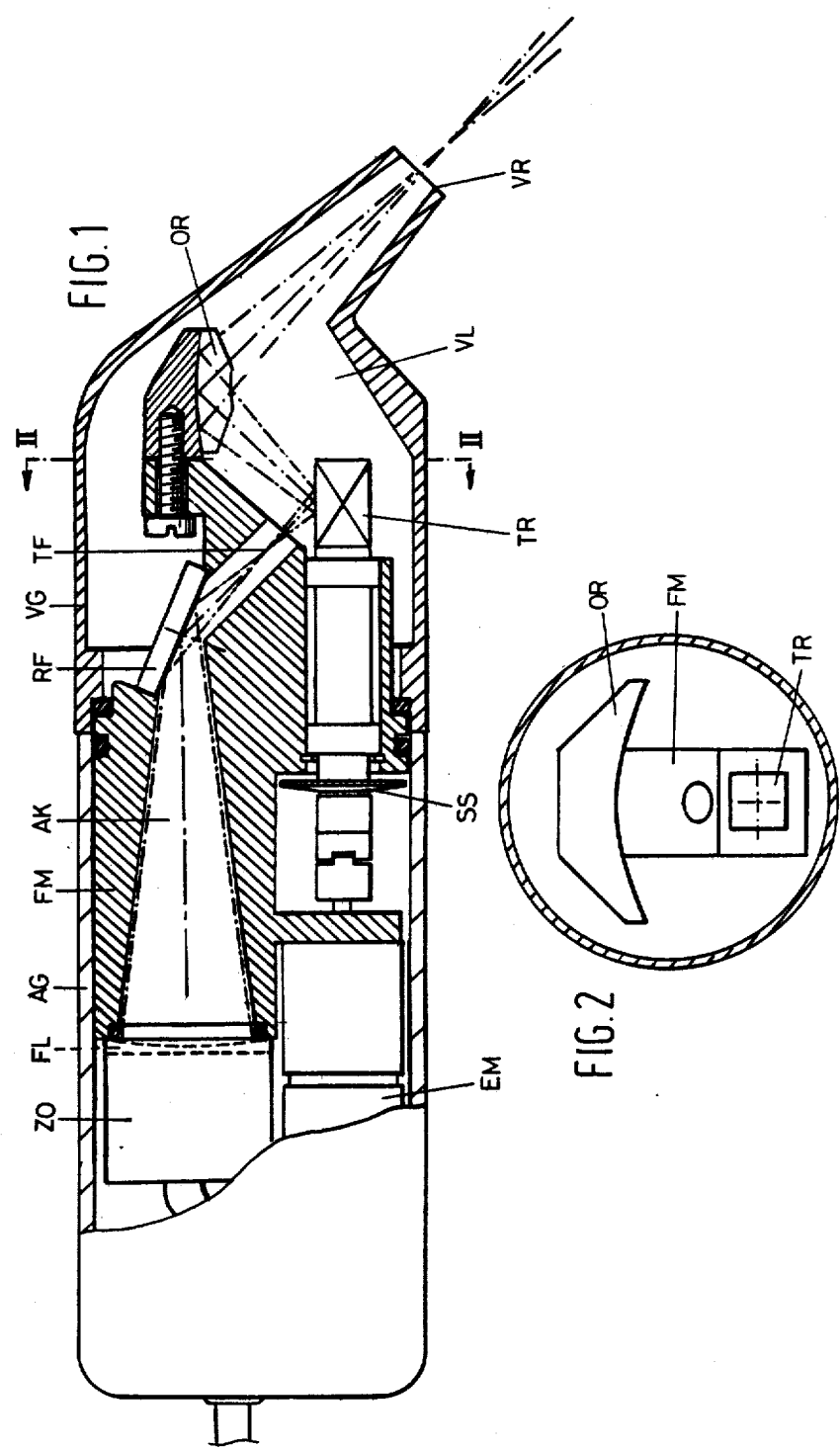

SCANNER FOR SCANNING AN OBJECT BY MEANS OF ULTRASONIC RADIATION

This invention relates to a scanner for scanning an object by means of ultrasonic radiation. Such a scanner is commonly used for producing through pulse-echo techniques a two-dimensional image of a cross-sectional plane of an object to be examined.

To this end, successive ultrasonic pulses are transmitted in the form of relatively narrow beams to the object under examination in accordance with such a pattern that a sufficiently detailed image of the relevant cross-section of the object can be formed from the different echo signals received. Known per se techniques may be used for recording, processing and/or reproducing the reflected echo signals.

A scanner to which the present invention relates comprises a housing adapted to contain a transmission medium for ultrasonic vibrations, which housing includes: transducer means for transmitting and receiving ultrasonic vibrations; a plurality of reflectors at least one of which is mounted for movement relative to the housing and functions as a scanning reflector and another of which functions as an object reflector; and focussing means for focussing ultrasonic waves, so that a beam of ultrasonic vibrations focussed by the focussing means and reflected by the object reflector to the object performs a scanning motion in response to movement of the scanning reflector.

Such a device, except for the aforesaid focussing means, is known from German Gebrauchsmuster No. 1,860,245, which discloses a scanner of the type described above. In this prior art device, the ultrasonic beam originating from fixedly mounted transducer means is so moved via a reflector, which reflector is mounted at an angle relative to the focal line of a parabolically curved, cylindrical reflector and is adapted to rotate about this focal line, that a so-called linear scan is produced.

A drawback inherent in this prior device is that the ultrasonic beam reflected by the object will be incident on at least one point of the object reflector at an approximately right angle. As a result, special steps will have to be taken in order to prevent parasitic, non-geometric reflections, i.e. spurious reflections not caused by the geometry of the object under examination.

A scanner in which an effort is made to reduce the last-named effect is disclosed in U.S. Pat. No. 4,208,602. This patent application discloses a device in which the beam movement required for scanning the object is achieved by using a swivelling reflector, resulting in the production of a sector scan. The occurrence of parasitic, non-geometric reflections in this device is prevented by a specific choice of the material and structure of the object reflector. This results in a large-size arrangement. Moreover, when performing examinations of rapidly varying objects, the then-required rapid swivelling of the object reflector may cause troublesome vibrations degrading the quality of the image. This drawback is all the more serious on account of the requirement that, to achieve adequate sensitivity, the surface area of the moving object reflector should be sufficiently large in order to reflect substantially all of the ultrasonic energy transmitted.

A scanner of the above type is further known from U.S. Pat. No. 4,185,501. This patent discloses a scanner of the sector scan type. In this prior device, a disc rotatable about a shaft and having a plurality of lens/reflector combinations peripherally mounted thereon is rotated about this shaft along a fixedly mounted transducer. Ultrasonic radiation emitting from this transducer can be bundled by such a lens/reflector combination when the latter is in the operative range of the transducer and reflected to the object reflector fixedly mounted in the housing, which object reflector is a flat surface.

In fact, a succession of mutually parallel beams of ultrasonic radiation is formed by the lens of a respective lens/reflector combination during the latter's movement about the transducer, each of such beams being directed by the reflector of the respective lens/reflector combination from a point on this reflector as determined by the instantaneous angular position of the disc to the fixedly mounted object reflector.

The resultant arrangement is relatively large and heavy. As a result of, inter alia, the contour of the device as dictated by the use of the rotary disc, this device permits only limited tilting movement relative to the object to be examined. Moreover, a rotation of the device relative to the object will produce a gyroscopic effect additionally impeding the handling thereof. Furthermore, provisions need be made to absorb ultrasonic energy, which implies that multiple and interfering echo images may be expected. Finally, the prior art arrangement cannot be simply modified so that a linear scan instead of a sector scan is achieved.

In addition to the aforesaid drawbacks, the scanners described above have the drawback that, in general, it is not simple to alter the device so as to optimally conform to special requirements set by a user. Special reference is made in this respect to the optimum choice of the ultrasonic frequency band of the transducer means used and the manner of scanning. This is of particular importance for specialistic applications, when only small series of each version will be manufactured.

It is an object of the present invention to eliminate the aforesaid drawbacks inherent in the prior art scanners. In particular, it is an object of the invention to provide a scanner whose form and small dimensions permit a wide range of applications.

To this end, the following demands are imposed:

(1) it must be possible to shift the focal area of the ultrasonic beam in the object by simple means, whether in a dynamic manner or not;

(2) it must be possible to adapt the scanning area to the object area considered important and/or to the conditions under which the scanner is to be used;

(3) the image formed of the desired object area must be of eminent quality and free from interfering effects caused, for example, by parasitic, non-geometric reflections;

(4) the structure of the scanner must permit simple adaptation to a desired mode of application, for example one requiring operation in a selected frequency range;

(5) the losses when forming the ultrasonic beam must be minimized;

(6) the quality of the image must not be degraded by vibrations generated by the device itself; and (7) a relatively high image rate of, for example, approximately 50 images per second must be possible.

A scanner according to the invention is characterized in that the focussing means include first focussing means adapted to form a first focus located within the space enclosed by the housing, and second focussing means adapted to project this first focus into the object.

As a scanner according to the invention is adapted to form such a first focus, it is possible to adjust the depth of field of the scanning beam throughout a wide range in a relatively simple manner. To this end, the scanner according to the invention is further characterized in that the first focussing means is adjustable so that the location of the first focus can be optionally shifted on the main axis of the transmission path between the transducer means and the object reflector. In this manner, a small displacement of the first focus relative to the object reflector results in a relatively large displacement of the area of "optimum depth of field".

The object reflector in such a scanner according to the invention is characterized in that it is formed so that the ultrasonic beam reflected thereby is focussed in two mutually perpendicular planes. As the scanner according to the invention is adapted for forming the first focus, it is possible to keep the dimensions of the scanning reflector small if this reflector can be positioned in the vicinity of this first focus. This is a major advantage over prior scanners in which such a first focus is not formed.

Therefore, the scanner according to the invention is further characterized in that the scanning reflector is a body defined by a plurality of reflector surfaces, the area of each of these reflector surfaces being small in comparison with the area of the active surface of the transducer means and the absolute aperture total surface area of a transducer, reflector or lens of each of these reflector surfaces being reduced relative to the absolute aperture of the transducer means in accordance with a ratio determined by the location of the first focus.

In general, moreover, it is desirable that the scanner should scan a relevant object area in an optimally favourable manner. This means that the scanner should allow the user to choose between scanning the object area in accordance with a sector-shaped, a trapezoidal or a rectangular pattern, depending on the relevant circumstances.

The scanner according to the invention can be simply adapted for any of these scanning modes. To this end, the object reflector is detachably mounted in the housing. This permits replacing the object reflector by one having the desired characteristics. Due to the manner in which the object reflector is arranged, the position which the scanning reflector mounted for rotation at a fixed place within the housing has relative to the object reflector, particularly the focal line thereof, can be optionally established. In dependence upon the thus-established position, the scanner is operative in accordance with one of the selected scanning modes.

The arrangement of the object reflector is further decisive of the place where the ultrasonic beam is focussed in the object. Consequently, by adjusting the first focussing means and/or the dimensions of the object reflector, the focal area of the ultrasonic beam can be located at a desired place within the object area.

The scanner according to the invention is further characterized in that a cavity for guiding the ultrasonic beam is formed in the housing, which cavity is shaped to at least partly follow the outline of the beam in longitudinal direction.

The scanner according to the invention is further characterized in that the reflective surfaces along the transmission path of the ultrasonic beam in the housing are positioned so that the sine of the angle at which this beam strikes these surfaces is greater than the quotient of the propagation velocity of the ultrasonic vibrations in the respective transmission medium and the propagation velocity of the ultrasonic vibrations in the respective solid material of these surfaces.

In this manner, transmission losses are minimized and false reflections are prevented from occurring.

The invention will be described in greater detail hereinafter with reference to the accompanying drawings, in which:

FIG. 1, combining a partly cross-sectional view with an interior view, shows an embodiment of a scanner according to the invention; and FIG. 2 shows a cross-sectional view taken along line II—II in FIG. 1.

Self-evidently, the invention is not limited to the embodiment shown in the drawings. The drawings show a frame FM, to which frame all of the other components are attached either directly or indirectly. This frame is enclosed by a housing adapted to contain a transmission medium for ultrasonic vibrations, which housing includes a rear section AG and a front section VG. If desired, the front section may be sealed in liquid-tight fashion by means of a window VR that is transparent to ultrasonic waves.

An acoustic channel AK is provided in the frame, which channel functions as a transmission path for the ultrasonic waves. This channel has its one end terminated by a transceiver unit ZO for transmitting and receiving ultrasonic waves, which transceiver unit can be simply replaced by a similar unit having a different rate of vibration. The acoustic channel has its other end in open communication with the chamber VL defined by the front section VG. Chamber VL houses a rotatable scanning reflector TR having a plurality of mutually identical reflector surfaces and a stationary object reflector OR detachably secured to the frame. The latter arrangement permits the object reflector to be simply replaced by one having different characteristics.

In the embodiment shown, the transceiver unit is a cylindrical body comprising a cylindrical transducer and a focussing lens FL disposed against the head face thereof, by means of which lens ultrasonic waves produced by the transceiver unit are united into a conical beam that is focussed in an intermediate or first focus TF. Seen in the direction away from the transceiver unit, the shape of the portion of the acoustic channel AK between the focussing lens FL and a stationary reflector RF is adapted to the shape of the beam. The location of the first focus can be optionally varied. For example, either by a selected setting of the focussing lens FL or by a dynamic adjustment of this lens, the location of this first focus can be varied either statically or dynamically. In principle, it is possible also to focus the beam so that the first focus is located in the part of the transmission path between the scanning reflector TR and the object reflector OR.

In the embodiment described the composite scanning reflector TR comprises four identical, rectangular, flat surfaces mounted normal to one another and spaced identical distances from the axis of rotation.

Within the scope of the present invention, other constructions of the scanning reflector are possible provided the condition be satisfied that during each sweep all of the reflector surfaces along a fixedly mounted object reflector is scanned each time one and the same object area is irradiated. By the choice of the curvature of the reflective surface of the object reflector OR in planes normal to the plane of the drawing of FIG. 1 and by the positioning of the scanning reflector relative to this object reflector (see also FIG. 2), it can be accomplished that a beam received by the object reflector from the scanning reflector during the rotation of the latter relative to the former is reflected so that a sequence of beams of equal direction is transmitted towards the window VR. The device is thus operative as a linear scanner. If desired, by altering the relative disposition of the object reflector and the scanning reflector, as well as the construction of the object reflector and/or the scanning reflector, the scanner can be adapted for operation as, for example, a sector scanner or a scanner scanning in accordance with a trapezoidal pattern.

The curvature of the object reflector in the plane of the drawing of FIG. 2 further results in a focussing of a divergent beam received from the scanning reflector. In order to achieve a similar focussing in a direction transverse to the first-meant direction, the object reflector is curved in planes parallel to the plane of the drawing of FIG. 1 too.

The scanning reflector TR which is bearing mounted in liquid-tight fashion, can be rotated through a coupling, a transmission mechanism and an electric motor EM. A synchronizing disc SS is mounted on the shaft for providing signals to be used for speed control and synchronization purposes.

The acoustic channel AK and the chamber VL are filled with a liquid capable of transmitting ultrasonic energy, for example water.

In accordance with a feature of the invention, the geometry of the transmission path for ultrasonic waves between the transceiver unit ZO and the exit of the chamber VL is such that ultrasonic vibrations propagating in the liquid can strike a portion of the boundary of this transmission path only at such an angle that total reflection occurs at the respective junction of liquid and reflective surfaces along the transmission path boundary. Such total reflection will occur if the sine of the angle at which the ultrasonic vibrations propagating in the liquid strike the respective surface of the transmission path boundary is greater than the quotient of the propagation velocity of ultrasonic vibrations in the liquid and the velocity at which the transversal ultrasonic waves propagate in the solid material of this surface of the transmission path boundary.

As all of the reflectors present in the transmission path are positioned to satisfy the aforesaid condition, no reflection losses occur in a scanner according to the invention, while the resultant image is free from false reflections.

By means of a configuration of the type shown in FIG. 1 it is possible to achieve a relatively large area of optimum depth of field in the object area. If desired, this area of optimum depth of field may be shifted in axial direction of the beam by varying the adjustment of the focussing lens FL and/or the position of the transceiver unit ZO.

We claim:

1. An ultrasonic scanner comprising:
a housing; one or more movable reflector means positioned within said housing; transducer means mounted within said housing and positioned to direct a beam of ultrasonic waves towards the surface of one of said movable reflector means; means for conducting said beam of ultrasonic waves; object reflector means mounted within said housing and positioned to receive ultrasonic waves reflected from said movable reflector means; first focussing means within said housing and adapted to converge said beam of ultrasonic waves to a first point within said housing at a preselected short distance from the one of said movable reflector means which receives the beam of ultrasonic waves, said object reflector means comprising a second focussing means for forming a second focus of said beam of ultrasonic waves within an object being scanned support means for supporting said movable reflector means, and for causing said movable refector means to traverse an arcuate path with respect to said object reflector means, whereby a beam of ultrasonic waves focussed within the object by said second focussing means performs a scanning motion in response to movement of said movable reflector means 2. The scanner as defined in claim 1 wherein said object reflector means is disposed whereby said ultrasonic waves reflected thereby are focused in two mutually perpendicular planes.

3. The scanner as defined in claim 2 wherein said first focussing means and is detachably mounted with said housing.

4. The ultrasonic scanner as defined in claim 3 wherein said one or more movable reflector means comprises a body defined by a plurality of reflector surfaces, the area of each one of said reflector surfaces being small relative to the surface area of said transducer means, and the absolute aperture of each one of said reflector surfaces being reduced relative to the absolute aperture of said transducer means in proportion to a ratio determined by the location of said first point.

5. The ultrasonic scanner as defined in claim 2 wherein said one or more movable reflector means comprises a body defined by a plurality of reflector surfaces, the area of each one of said reflector surfaces being small relative to the surface area of said transducer means, and the absolute aperture of each one of said reflector surfaces being reduced relative to the absolute aperture of said transducer means in proportion to a ratio determined by the location of said first point.

6. The scanner as defined in claim 1 wherein said object reflector means is detachably mounted within said housing.

7. The scanner as defined in claim 1 wherein said first focussing means is detachably mounted with said housing.

8. The ultrasonic scanner as defined in claim 7 wherein said one or more movable reflector means comprises a body by a plurality of reflector surfaces, the area of each one of said reflector being small relative to the surface area of said transducer means, and the absolute aperture of each one of said reflector surfaces being reduced relative to the absolute aperture of said transducer means in proportion to a ratio determined by the location of said first point.

9. The ultrasonic scanner as defined in claim 1 wherein said one or more movable reflector means comprises a body defined by a plurality of reflector surfaces, the area of each one of said reflector surfaces being small relative to the surface area of said transducer means, and the absolute aperture of each one of said reflector surfaces being reduced relative to the absolute aperture of said transducer means in proportion to a ratio determined by the location of said first point.

10. The ultrasonic scanner as defined in claim 9 wherein said means for conducting said ultrasonic waves comprises reflective surfaces which are disposed relative to a beam of said ultrasonic waves in such a manner that the sine of the angle at which said beam impinges on said surfaces exceeds the ratio of the propagation velocity of said ultrasonic waves within the respective transmission medium within said housing, and the propagation velocity of the ultrasonic waves within the respective solid material comprising said reflective surfaces.

11. The ultrasonic scanner as defined in claim 1 wherein said means for conducting said ultrasonic waves includes reflective surfaces which are disposed relative to a beam of said ultrasonic waves in such a manner that the sine of the angle at which said beam of said ultrasonic waves impinges on said surfaces exceeds the ratio of the propagation velocity of said ultrasonic waves within a respective transmission medium within said housing, and the propagation velocity of the ultrasonic waves within the respective solid material comprising said reflective surfaces.

12. An ultrasonic scanner comprising: a housing; one or more movable reflector means positioned within said housing; transducer means mounted within said housing and positioned to direct a beam of ultrasonic waves towards the surface of one of said movable reflector means; means for conducting said beam of ultrasonic waves; object reflector means mounted within said housing and positioned to receive ultrasonic waves reflected from said movable reflector means; first focussing means mounted within said housing and adapted to converge said beam of ultrasonic waves to a first point within said housing, said first focussing means being adjustable for selectively positioning said first point a preselected short distance from the one of said movable reflector means which receives ultrasonic waves, said object reflector means comprising a second focussing means for forming a second focus of said beam of ultrasonic waves within an object being scanned support means for supporting said movable reflector means, and for causing said movable reflector means to transverse an arcuate path with respect to said object reflector means, whereby a beam of ultrasonic waves focussed within the object by said second focussing means performs a scanning motion in response to movement of said movable reflector means.

13. The scanner as defined in claim 12 wherein said object reflector means is disposed whereby said ultrasonic waves reflected thereby are focused in two mutually perpendicular planes.

14. The scanner as defined in claim 13 wherein said object reflector means is detachably mounted within said housing.

15. The ultrasonic scanner as defined in claim 13 wherein said one or more movable reflector means comprises a body defined by a plurality of reflector surfaces, the area of each one of said reflector surfaces being small relative to the surface area of said transducer means, and the absolute aperture of each one of said reflector surfaces being reduced relative to the absolute aperture of said transducer means in proportion to a ratio determined by the location of said first point.

16. The scanner as defined in claim 12 wherein said object reflector means is detachably mounted within said housing.

17. The scanner as defined in claim 12 wherein said first focussing means and is detachably mounted with said housing.

18. The ultrasonic scanner as defined in claim 17 wherein said one or more movable reflector means comprises a body defined by a plurality of reflector surfaces, the area of each one of said reflector surfaces being small relative to the surface area of said transducer means, and the absolute aperture of each one of said reflector surfaces being reduced relative to the absolute aperture of said transducer means in proportion to a ratio determined by the location of said first point.

19. The ultrasonic scanner as defined in claim 12 wherein said one or more movable reflector means comprises a body defined by a plurality of reflector surfaces, the area of each one of said reflector surfaces being small relative to the surface area of said transducer means, and the absolute aperture of each one of said reflector surfaces being reduced relative to the absolute aperture of said transducer means in proportion to a ratio determined by the location of said first point.

20. The ultrasonic scanner as defined in claim 12 wherein said means for conducting said ultrasonic waves includes reflective surfaces which are disposed relative to a beam of said ultrasonic waves in such a manner that the sine of the angle at which said beam of said ultrasonic waves impinges on said surfaces exceeds the ratio of the propagation velocity of said ultrasonic waves within a respective transmission medium within said housing, and the propagation velocity of the ultrasonic waves within the respective solid material comprising said reflective surfaces.

* * * * *

UNITED STATES PATENT AND TRADEMARK OFFICE
CERTIFICATE OF CORRECTION

PATENT NO. : 4,466,286

DATED : AUGUST 21, 1984

INVENTOR(S) : BERBEÉ, VOÛTE and THIJSSEN

It is certified that error appears in the above-identified patent and that said Letters Patent is hereby corrected as shown below:

Column 6, line 1, after "means" insert -- mounted --;
          line 9, after "scanned" insert a -- semicolon(;) --;

Column 7, line 28, "conduting" should read -- conducting --;
          line 40, after "scanned" insert a -- semicolon(;) --;

Column 8, line 18, after "means" delete "and".

Signed and Sealed this

Twelfth Day of March 1985

[SEAL]

Attest:

DONALD J. QUIGG

*Attesting Officer*     *Acting Commissioner of Patents and Trademarks*